US00PP28367P3

(12) United States Plant Patent
Zaiger et al.

(10) Patent No.: US PP28,367 P3
(45) Date of Patent: Sep. 12, 2017

(54) INTERSPECIFIC TREE NAMED 'CARLSBAD'

(50) Latin Name: ***Interspecific Prunus* species**
Varietal Denomination: Carlsbad

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 108 days.

(21) Appl. No.: 14/757,347

(22) Filed: Dec. 21, 2015

(65) Prior Publication Data

US 2017/0181343 P1 Jun. 22, 2017

(51) Int. Cl.
*A01H 5/08* (2006.01)

(52) U.S. Cl.
USPC ..... Plt./180

(58) Field of Classification Search
USPC ..... Plt./156, 180
See application file for complete search history.

*Primary Examiner* — Susan McCormick Ewoldt
*Assistant Examiner* — Karen Redden

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, semi-spreading growth habit.
2. Tree being a regular and productive bearer of large size fruit.
3. Fruit with an attractive orange skin color.
4. Fruit with good flavor and eating quality.
5. Fruit with good handling and shipping quality.

1 Drawing Sheet

Botanical designation: Interspecific *Prunus* species.
Variety denomination: 'Carlsbad'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Honey Rich' Interspecific (U.S. Plant Pat. No. 10,292), 'Kylese' Interspecific (U.S. Plant Pat. No. 23,123) and our non-patented proprietary interspecific seedlings with the field identification numbers '29ZH154', '10MA521', '3ZC416', '176LM586', '9ZC962' and '289LF578'.

STATEMENT REGARDING FEDERALLY SPONSORED RESEARCH AND DEVELOPMENT

Not applicable.

ORIGIN OF THE VARIETY

The new and distinct variety of interspecific tree, consists of crosses between the following species *Prunus armeniaca, Prunus salicina* and *Prunus persica*. It was originated by us in our experimental orchard located near Modesto, Calif. as a first generation cross between our proprietary non-patented interspecific seedlings with field identification numbers '29ZH154' and '10MA521'. The non-patented interspecific seed parent (29ZH154) originated from the cross of our proprietary non-patented interspecific seedlings '3ZC416' and '176LM586'. The non-patented interspecific pollen parent (10MA521) originated as an open pollinated seedling selection from our proprietary non-patented interspecific seedling '9ZC962' which is a first generation cross of 'Honey Rich' Interspecific (U.S. Plant Pat. No. 10,292) and our non-patented interspecific seedling '289LF578'. A large number of these first generation seedlings were budded onto older established trees of 'Nemaguard' Rootstock (non-patented) to enhance earlier fruit production. Under close and careful observation the present budded seedling exhibited desirable fruit and tree characteristics and was selected in 2011 for additional asexual propagation and commercialization.

ASEXUAL REPRODUCTION OF THE VARIETY

In 2011 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of interspecific tree which consists of multiple crosses between Apricots, Plums and Peaches is of large size, vigorous, semi-spreading growth and a regular and productive bearer of large size, yellow-orange flesh, freestone fruit. The fruit is further characterized by having an attractive orange skin color, good flavor and eating quality and having good storage and shipping quality. In comparison to its non-patented interspecific seed parent '29ZH154' the fruit of the new variety is larger in size and is approximately 19 days earlier in maturity. In comparison to its non-patented interspecific pollen parent '10MA521' the fruit of the new variety has yellow-orange flesh compared to orange and is approximately 23 days earlier in maturity. In comparison to the commercial variety 'Kylese' Interspecific (U.S. Plant Pat. No. 23,123) the fruit of the new variety is larger in size and is approximately 5 days earlier in maturity.

DESCRIPTION OF PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color published in 1958.

Tree:

- *Size*.—Large, usually pruned to 3 to 3.5 meters in height and width for economical harvesting of fruit. Size varies with different cultural practices.
- *Vigor*.—Vigorous, growth of 1.5 to 2 meters the first growing season. Varies slightly with type and fertility of soil, climatic conditions and cultural practices.
- *Form*.—Semi-spreading, usually pruned to vase shape.
- *Branching habit*.—Semi-spreading, crotch angle approximately 30°, increases with heavy crop load.
- *Productivity*.—Productive, thinning and spacing necessary for desired market size fruit. Number of fruit set varies with climatic conditions during blooming period.
- *Bearer*.—Regular, has had adequate fruit set 3 consecutive years. No alternate bearing observed.
- *Fertility*.—Self fertile, adequate fruit set under bagged limbs.
- *Density*.—Medium dense, pruned to vase shape to increase air movement and sunlight to center of tree to enhance fruit color and health of fruit spurs.
- *Hardiness*.—Hardy in all stone fruit growing areas of California. Tree grown in USDA Hardiness Zone 9. Winter chilling requirement approximately 550 hours at or below 45° F.

Trunk:

- *Size*.—Large. Average circumference 61.0 cm at 25.0 cm above ground on a 5 year old tree.
- *Stocky*.—Medium stocky.
- *Texture*.—Medium shaggy, roughness increases with age.
- *Color*.—Varies from 2.5Y 6/2 to 2.5Y 5/2.

Branches:

- *Size*.—Medium. Average circumference 14.2 cm at 1.2 meters above ground on a 5 year old tree. Crotch angle approximately 30°, increases with heavy crop load.
- *Surface texture*.—New growth relatively smooth. Mature growth medium rough, roughness increases with age.
- *Lenticels*.—Average number 47 in a 25.8 square cm area. Average length 3.6 mm. Average width 1.6 mm. Color varies from 10YR 6/2 to 2.5Y 6/10.
- *Color*.—New growth varies from 5GY 4/8 to 5R 3/4. Older growth varies from 5YR 3/2 to 5YR 2/2, varies with age of growth.

Leaves:

- *Size*.—Medium to large. Average length 70.8 mm. Average width 60.3 mm.
- *Form*.—Ovate.
- *Apex*.—Acuminate.
- *Base*.—Cuneate.
- *Margin*.—Serrulate.
- *Thickness*.—Medium.
- *Surface texture*.—Upper surface relatively smooth, slight indentations over midrib and leaf veins. Lower surface relatively smooth, except for small ridges created by midrib and pinnate venation. Both upper and lower surfaces glabrous.
- *Petiole*.—Large. Average length 21.4 mm. Average width 1.2 mm. Longitudinally grooved. Surface — glabrous. Color varies from 5GY 6/6 to 7.5R 2/6.
- *Glands*.—Type — reniform. Size — small. Average length 0.6 mm. Average diameter 0.5 mm. Average number 3, varies from 2 to 4. Located primarily on the upper portion of the petiole and base of leaf blade. Color 7.5R 2/6.
- *Stipules*.—Average length 7.0 mm. Average number 2. Edges — pectinate. Color varies from 5GY 6/6 to 5GY 6/8.
- *Color*.—Upper surface varies from 5GY 3/4 to 7.5GY 2/4. Lower surface varies from 5GY 4/4 to 5GY 3/4. Midvein color varies from 5GY 7/6 to 5GY 4/6.

Flower buds:

- *Size*.—Medium to large. Average length 14.8 mm. Average diameter 9.1 mm.
- *Hardiness*.—Hardy with respect to California winters.
- *Form*.—Conical, becoming elongated just before opening.
- *Pedicel*.—Average length 2.0 mm. Average width 1.8 mm. Color varies from 2.5GY 7/6 to 2.5GY 6/6. Surface — glabrous.
- *Color*.—Varies from 5RP 8/4 to 7.5RP 7/8.
- *Number of buds per spur*.—Varies from 7 to 16, average 10. Varies with age of spur.

Flowers:

*Blooming period*.—Date of First Bloom Feb. 13, 2015. Date of Petal Fall Feb. 23, 2015, varies slightly with climatic conditions.

*Size*.—Medium. Average height 14.0 mm. Average diameter 23.1 mm.

*Petals*.—Normally 5, alternately arranged to sepals. Size — medium to large. Average length 12.5 mm. Average width 14.3 mm. Form — orbicular. Arrangement — overlapping. Margin — sinuate. Petal apex — rounded. Petal base — truncated. Color varies from 5RP 9/2 to 7.5RP 9/2. Both upper and lower surfaces glabrous.

*Sepals*.—Normally 5, alternately arranged to petals. Size — medium to large. Average length 6.5 mm. Average width 5.3 mm. Apex — rounded to triangular. Shape — triangular. Margin — entire. Both upper and lower surfaces glabrous. Color — upper surface varies from 2.5R 3/6 to 2.5R 3/8. Lower surface varies from 2.5R 3/8 to 5R 2/8.

*Stamens*.—Average number per flower 28. Average filament length 9.1 mm. Filament color N 9.5/(white). Anther color varies from 5Y 8/8 to 7.5Y 8/8.

*Pollen*.—Self fertile, adequate fruit set under bagged limbs. Color varies from 5Y 8/10 to 5Y 7/10.

*Pistil*.—Number — normally one. Average length 14.0 mm. Position of stigma even with anthers. Surface — pubescent. Color varies from 10Y 8.5/4 to 10Y 8/6.

*Fragrance*.—Wanting.

*Color*.—Varies from 7.5RP 9/2 to 10RP 9/2.

*Number flowers per flower bud*.—Average 4, varies from 2 to 5.

*Pedicel*.—Average length 2.7 mm. Average width 1.7 mm. Color varies from 10Y 7/6 to 2.5GY 7/6. Surface — glabrous.

Fruit:

*Maturity when described*.—Firm ripe and ready for consumption.

*Date of first picking*.—May 5, 2015.

*Date of last picking*.—May 15, 2015, varies slightly with climatic conditions.

*Size*.—Large. Average diameter axially 60.6 mm. Average transversely in suture plane 64.2 mm. Average across suture plane 63.7 mm. Average weight 147.7 grams, varies slightly with fertility of the soil, amount of thinning and climatic conditions.

*Form*.—Globose to slightly elongated.

*Suture*.—Lipped.

*Ventral surface*.—Lipped.

*Apex*.—Retuse.

*Base*.—Retuse.

*Stem cavity*.—Rounded to slightly elongated in suture plane. Average depth 7.3 mm. Average diameter 3.5 mm.

Stem:

*Size*.—Small to medium. Average length 7.3 mm. Average diameter 3.5 mm.

*Color*.—Varies from 2.5GY 6/8 to 2.5GY 5/6.

Flesh:

*Ripens*.—Evenly.

*Texture*.—Firm, meaty.

*Fibers*.—Few, small, tender.

*Firmness*.—Firm, comparable to other commercial interspecific apricot varieties.

*Aroma*.—Moderate.

*Amydgalin*.—Undetected.

*Eating quality*.—Good.

*Flavor*.—Good, with a good balance between acid and sugar.

*Juice*.—Heavy amount, enhances flavor.

*Brix*.—Average Brix 12.2°.

*Color*.—Varies from 2.5Y 8.5/8 to 10YR 6/10.

*Pit color*.—Average length 38.0 mm. Average width 28.7 mm. Average depth 9.0 mm. Color varies from 10YR 6/6 to 7.5YR 6/6.

Skin:

*Thickness*.—Medium.

*Surface*.—Slightly waffled.

*Pubescence*.—Moderate pubescence, short in length.

*Tendency to crack*.—None.

*Color*.—Ground color varies from 10YR 7/10 to 7.5YR 6/10. Overspread with 7.5YR 5/10 to 5YR 5/10.

*Tenacity*.—Tenacious to flesh.

*Astringency*.—Undetected.

Stone:

*Type*.—Freestone, weak adherence.

*Size*.—Large. Average length 36.3 mm. Average width 26.7 mm. Average thickness 14.6 mm.

*Form*.—Ovoid.

*Base*.—Flat.

*Apex*.—Round.

*Surface*.—Lightly pitted throughout. One shallow groove on each side of suture extending from base toward apex.

*Sides*.—Unequal, one side extending further outward from suture plane.

*Ridges*.—Very small and short, extending from base towards apex.

*Tendency to split*.—None.

*Color*.—Varies from 2.5YR 2/4 to 2.5YR 3/4 when dry.

Kernel:

*Size*.—Large. Average length 19.7 mm. Average width 13.5 mm. Average depth 6.9 mm.

*Form*.—Ovoid.

*Viability*.—Viable, complete embryo development.

*Skin color*.—Varies from 2.5Y 8.5/4 to 5Y 9/2.

Use:

*Dessert*.—Market — local and long distance.

Keeping quality: Good, held firm in cold storage at 38° to 42° F. for 3 weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

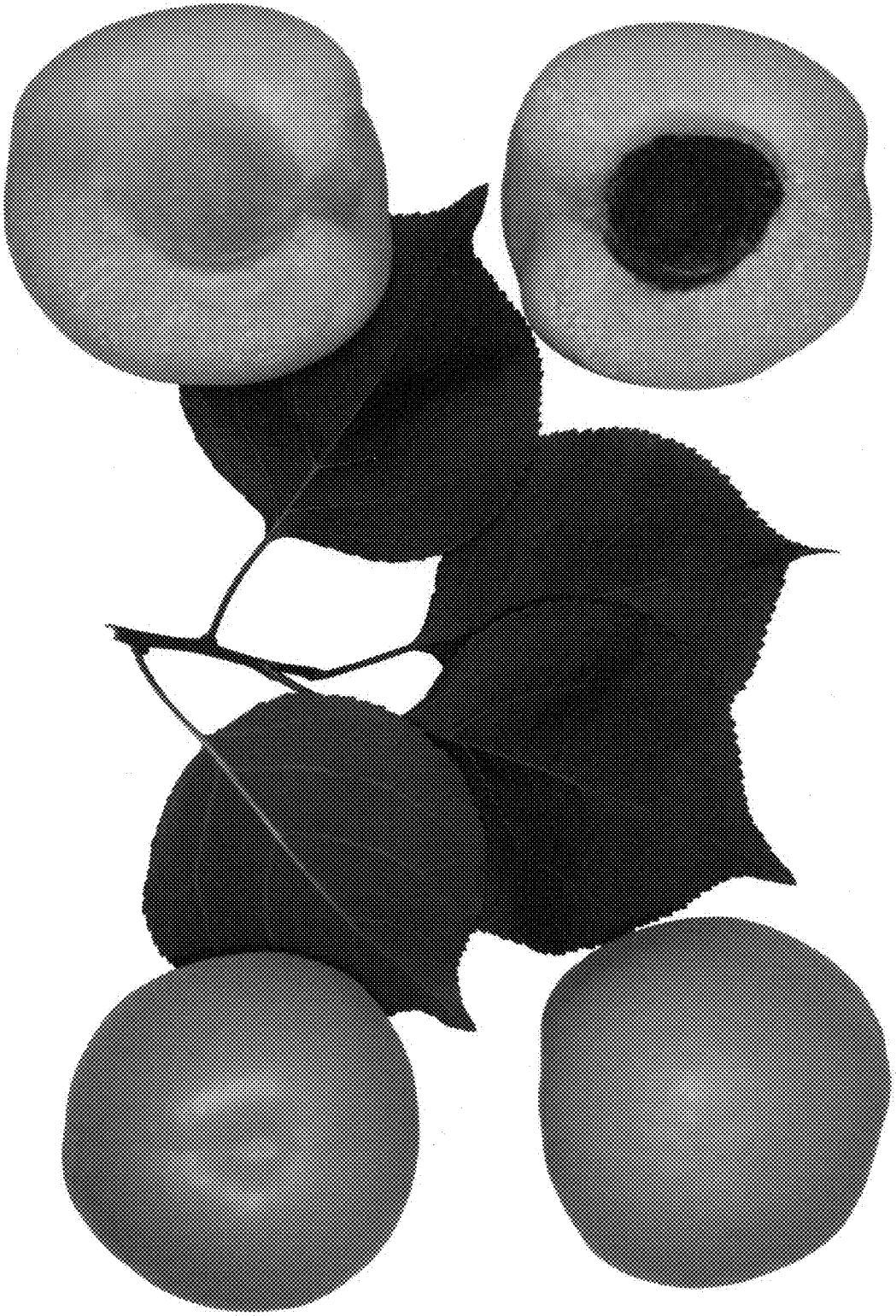

* * * * *